United States Patent
Dennis

(10) Patent No.: US 8,679,153 B2
(45) Date of Patent: Mar. 25, 2014

(54) METHOD AND APPARATUS FOR SURGICALLY CLOSING AN OPEN ABDOMEN

(76) Inventor: Andrew Dennis, Chicago, IL (US)

(*) Notice: Subject to any disclaimer, the term of this patent is extended or adjusted under 35 U.S.C. 154(b) by 410 days.

(21) Appl. No.: 13/188,549

(22) Filed: Jul. 22, 2011

(65) Prior Publication Data

US 2012/0029539 A1 Feb. 2, 2012

Related U.S. Application Data

(60) Provisional application No. 61/369,320, filed on Jul. 30, 2010.

(51) Int. Cl.
*A61B 17/08* (2006.01)

(52) U.S. Cl.
USPC .......................... 606/216; 606/213

(58) Field of Classification Search
USPC ................................ 606/213–216
See application file for complete search history.

(56) References Cited

U.S. PATENT DOCUMENTS

| | | | |
|---|---|---|---|
| 5,665,108 A | 9/1997 | Galindo | |
| 6,436,123 B1 | 8/2002 | Magovern | |
| 7,351,250 B2 | 4/2008 | Zamierowski | |
| 7,658,749 B2 | 2/2010 | Wittmann | |
| 7,662,169 B2 | 2/2010 | Wittmann | |
| 7,884,258 B2 | 2/2011 | Boehringer et al. | |
| 2002/0029063 A1 | 3/2002 | Wittmann | |
| 2004/0221431 A1 | 11/2004 | Wittmann | |
| 2005/0273066 A1 | 12/2005 | Wittmann | |
| 2009/0270999 A1 | 10/2009 | Brown | |
| 2010/0114160 A1 | 5/2010 | Wittmann | |
| 2010/0256674 A1 | 10/2010 | Wittmann | |

OTHER PUBLICATIONS

Keramati M, Srivastava A, Sakabu S, Rumbolo P, Smock M, Pollack J, Troop B The Wittmann Patch as a temporary abdominal closure device after decompressive celiotomy for abdominal compartment syndrome following burn. Burns. Jun. 2008; 34(4):493-7.
Tieu BH, Cho SD, Luem N, Riha G, Mayberry J, Schreiber MA. The use of the Wittmann Patch facilitates a high rate of fascial closure in severely injured trauma patients and critically ill emergency surgery patients. J Trauma. Oct. 2008; 65(4):865-70.
Aprahamian C, Wittmann DH, Bergstein JM, Bergstein JM, Sasse EA, Wittmann DH. Temporary abdominal closure (TAC) for planned relaparotomy (etappenlavage) in trauma. J Trauma. 1990; 30:719-723.
Miller PR, Meredith JW, Hohnson JC, Chang MC. Prospective evaluation of vacuum-assisted fascial closure after open abdomen. Planned ventral hernia rate is substantially reduced. Annals of Surgery vol. 239, May 5, 2004.
Cipolla J, Stawicki SP, Hoff WS, McQuay N, Hoey BA, Wainwright G, Grossman MD. A proposed algorithm for managing the open abdomen. Am Surg. Mar. 2005; 71 (3):202-7.

(Continued)

*Primary Examiner* — Gregory Anderson
(74) *Attorney, Agent, or Firm* — Teddy Scott, Jr.; Polsinelli PC

(57) ABSTRACT

An open abdomen wound as a result of injury or surgery is closed using fastener sheets, such as hook and loop fastener sheets, that are attached at opposing edges of the wound using bolsters through which surgical suture thread is passed to secure the abdominal wall between the fastener sheets and the bolsters. Tension forces are exerted on the fastener sheets and the sheets secured to one another in one or more steps drawing the wound edges toward one another. The tension forces are distributed by the bolsters to avoid loss of tissue at the wound edges. Successful closure of the wound is possible.

12 Claims, 7 Drawing Sheets

(56) References Cited

OTHER PUBLICATIONS

Hadeed JG, Staman GW, Sariol HS, Kumar S, Ross SE. Delayed primary closure in damage control laparotomy: the value of the Wittmann patch. Am Surg. Jan. 2007; 73(I): 10-2.

Wittmann DH, Aprahamian C, Bergstein JM, Edmiston CE, Frantzides CT, Quebbeman EJ, Condon RE. A burr-like device to facilitate temporary abdominal closure in planned multiple laparotomies. Eur J Surg. Feb. 1993; 159(2):75-9.

Weinberg JA, George RL, Griffin RL, Stewart AH, ReiffDA, Kerby JD, Melton SM, Rue LW 3rd. Closing the open abdomen: improved success with Wittmann Patch staged abdominal closure. J Trauma. Aug. 2008; 65(2):345-8..

Fantus RJ, Mellett MM, Kirby JP. Use of controlled fascial tension and an adhesion preventing barrier to achieve delayed primary fascial closure in patients managed with an open abdomen. Am J Surg. Aug. 2006; 192(2):243-7.

Van Hensbroek PB, Wind J, DijkgraafMGW, Busch ORC, Coslings JC. Temporary Closure of the open abdomen: a systematic review on delayed primary fascial closure in patients with an open abdomen. World J Surg. (2009) 33:199-207.

Bjorck, M. et al., Classification—Important Step to Improve Management of Patients with an Open Abdomen. World Journal of Surgery, (2009) 33:1154-1157.

Kaplan, M. et al., Guidelines for the Management of the Open Abdomen, Supplement to the Oct. 2005 Issue of Wounds: A Compendium of Clinical Research and Practice, 27 pgs.

Chow, S., Creative Wound Management of the Open Abdomen—Grant Medical Center, http://www.grantlifelink.com/traumacare2008/Day2Lectures/Creative%20Wound%20 Management%20of%20the%20Open%20Abdomen.pdf.

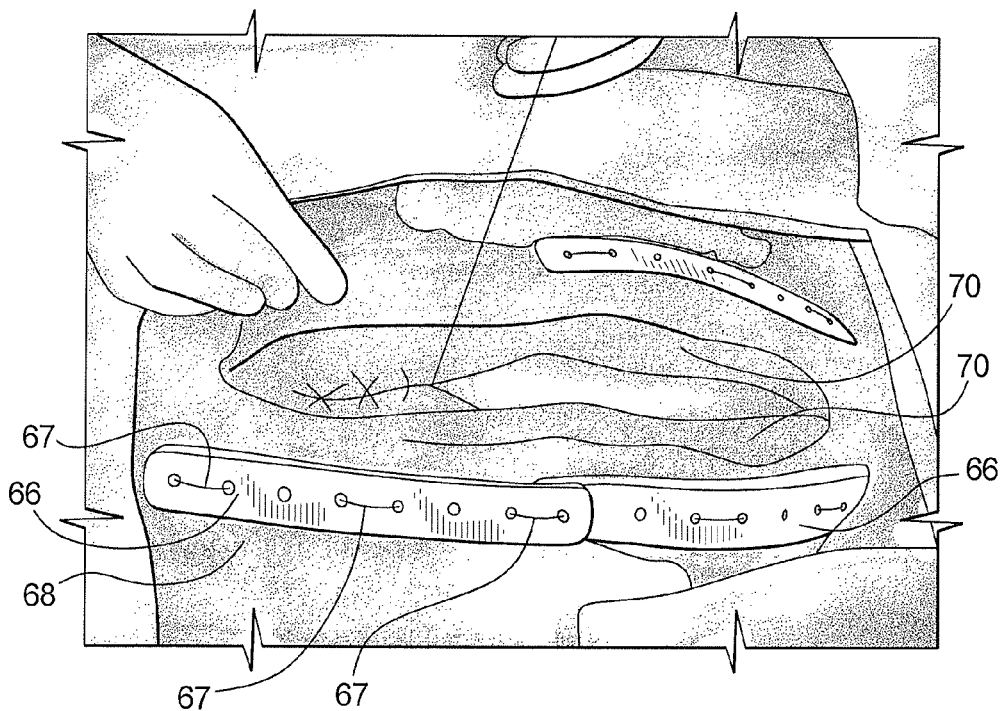
FIG. 13
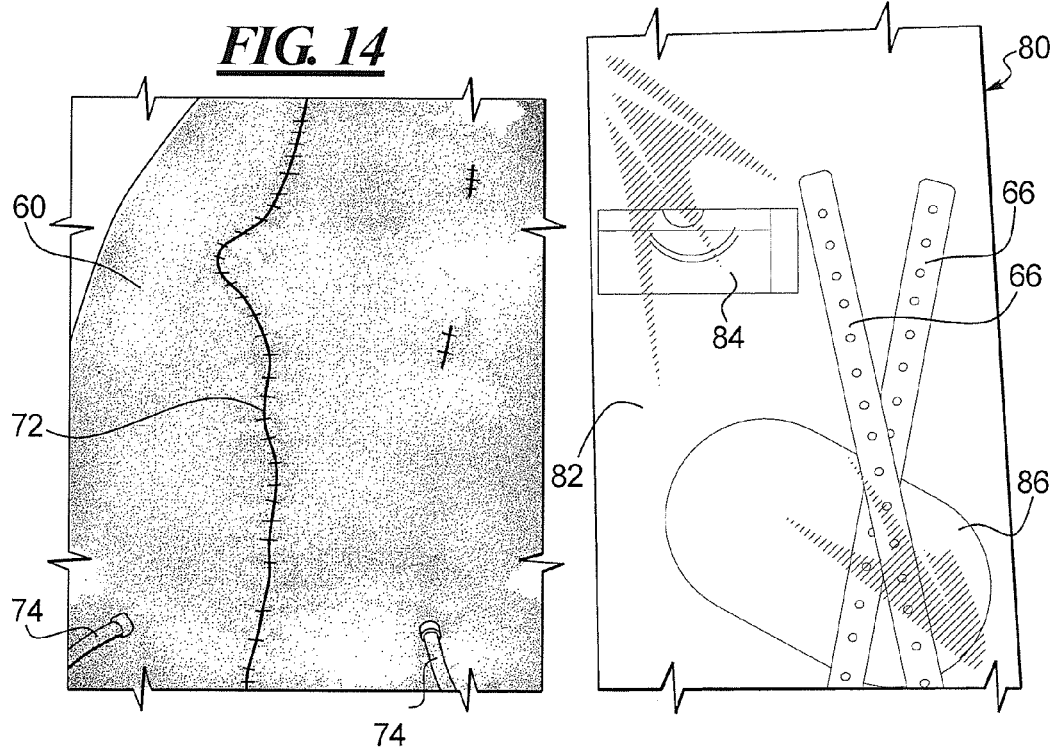
FIG. 14
FIG. 15

METHOD AND APPARATUS FOR SURGICALLY CLOSING AN OPEN ABDOMEN

CROSS-REFERENCE TO RELATED APPLICATION

This application claims the benefit of U.S. Provisional Patent Application Ser. No. 61/369,320, filed Jul. 30, 2010, which is incorporated herein by reference.

BACKGROUND OF THE INVENTION

1. Field of the Invention

The present invention relates generally to a method and apparatus for surgically closing an open abdomen of a patient, and more particularly to a method and apparatus for surgically closing acute and chronic open abdomen wounds.

2. Description of the Related Art

A variety of different medical conditions or accidental injuries can result in a patient having an open abdomen wound. For instance, in some medical conditions, the viscera within the abdomen swells which causes the viscera to be compressed by the abdominal wall of the person. Unless decompressed, the compression results in loss of circulation to the viscera and to tissue death, which may result in death of the patient. The pressure within the abdomen can be relieved by surgical opening of the abdomen, such as by a ventral incision, as a prophylactic procedure. While the risk of death and visceral tissue loss is decreased by the decompression while the tissues heal, the abdominal incision must be closed after the swelling decreases. The muscles of the abdominal wall, however, generally retract while the incision is open, pulling the wound open and preventing the wound from being closed. This is referred to as lost domain, and the result is a patient with an open abdominal wound, referred to as the complex open abdomen.

Injuries to the viscera such as from a gunshot or knife wound, vehicular accident or other injury can also cause swelling of the viscera, particularly where a surgical repair of the bowels, intestines and other organs are required. The act of operating on the abdominal tissues may also cause the tissues to swell or otherwise change in a way that causes issues in attempting to close the wound. At the conclusion of the surgery to repair the injury, the swelling as well as any muscle retraction prevents closure of wound in the abdominal wall. As a result, an open abdomen can result that is not immediately able to be surgically closed without risk to the patient. This is referred to as an acute open abdomen.

Contemporary surgeons struggle with the complex open abdomen. In years past, it was rare to have a persistently open abdomen. In contrast, for a number of reasons, contemporary practitioners routinely leave abdomens open after ceilotomy. Complex open abdomens are often the result of damage control laparotomy for trauma, decompression for abdominal compartment syndrome, and massive, possibly excessive, fluid resuscitations resulting in bowel and abdominal wall edema. It is estimated that up to one in nine patients undergoing laparotomy for trauma is not closed at the time of initial surgery.

In some patients who have had need for an open abdomen, the open wound has been closed by a skin graft, thus essentially forming a large ventral hernia on the abdomen. This is referred to as a chronic open abdomen. While the skin graft encloses the viscera within the skin, it does not provide the protection for the viscera that the muscles and other structures of the abdominal wall provide. The patient no longer has integrity of the abdominal wall, which may limit many of the activities that the patient may wish to engage in. In addition, the rectus muscles, those which allow one to flex the abdomen in doing a "sit up" type maneuver, end up very lateral and no longer attached to one another. By being so lateral and not bound to each other, the individual is unable to flex the torso, thus being functionally impaired.

Several options exist for the management of the increasingly common open abdomen wound. However, due to idiosyncratic complexities associated with this group of patients as well as institutional variability, no single technique can be universally employed to manage these cases. Current techniques include planned ventral hernia with placement of absorbable mesh and/or skin graft as noted above, vacuum assisted closure, complex abdominal wall repairs, and a variety of temporary closures with serial attempts at tightening. The complex repairs include component separation, in other words, separation of the muscles and other tissues in the abdominal wall from one another and connecting just some components together. Among the serial tightening techniques is the Wittmann Patch, which is an artificial bur which serves as a temporary abdominal fascial prosthesis in cases where the abdomen cannot be closed due to abdominal compartment syndrome or because multiple further operations are planned (staged abdominal repair). It consists of a sterile hook and a sterile loop sheet made from propylene or other polymer.

In particular, the Wittmann patch includes two sheets of a biocompatible polymer; one sheet is covered with micro hooks or mushrooms and the other with loops. These sheets have been traditionally sutured to the fascial edges of an open abdomen and then pressed together to adhere. When adhered to each other, these sheets can withstand shear forces similar to normal intact fascia. The patch sheets are sequentially trimmed and progressively pulled tighter across the open abdomen to slowly stretch the abdominal wall, regain domain and eventually re-approximate the fascia, or close the open wound.

In recent years, several doctors have reported improved success by combining the Wittmann Patch with vacuum assisted dressings. Doctors report following the same method of implanting the patch by sewing it directly to the fascial edge. Fixing the patch to the leading edge of the fascia places substantial force on a focused area of tissue. As a result, complications of fascial necrosis and tearing where the patch interfaces with the fascial edge are often reported. This loss of fascial integrity is sometimes of sufficient extent to cause patch failure. The tissues won't hold the suture. In an attempt to prevent tissue damage, less tension forces are applied to the patch so that it won't tear through the fascial wall where it has been sewn. More importantly, this method of Wittmann Patch fixation often sacrifices several centimeters of precious abdominal wall which could be used to restore abdominal integrity. The result may be a hernia rather than a successful closure of the abdominal wall structures.

The health of the patient plays a roll in the ability to close an open abdomen. For example, patients with a condition such as diabetes may have poor tissue quality at the abdominal wall anyway. Efforts to close the open abdomen can result in further tissue degradation.

Another approach has been to provide elastomeric bands that span the open wound. The elastomeric bands apply a dynamic tension to the tissues by exerting a dynamic pull on the muscles and other tissues.

SUMMARY OF THE INVENTION

The present invention provides a method and apparatus by which an open abdomen wound may be closed with little or no loss of the tissue at the fascial edge of the wound. In a patient with an open abdominal wound, or in a patient who has previously had an open abdominal wound that has been covered by a skin graft, for example, the abdominal wound is covered by a fastener sheet or sheets that is secured to the opposing edges of the wound by suturing through the abdominal walls. The fastener sheet is positioned under the abdominal wall. In a preferred embodiment, the fastener sheet extends laterally to the edge of the rectus muscle on either side of the wound. Bolsters are positioned at the outside of the abdominal wall. In a preferred embodiment, the bolsters are fastened over skin at the lateral edge of the rectus muscle. In one example, the bolsters are attached at approximately 2 inches from the wound edge.

A hydrocolloid adhesive dressing is preferably placed over the skin before positioning of the padded bolsters so that the dressing is between the bolster and the skin to protect the skin. Suture is passed through a bolster hole, through all layers of the abdominal wall, through the fastener sheet, back through the abdominal wall and through a different bolster hole and is tied. This process is repeated several times through each bolster to secure the abdominal wall between the underlying fastener sheet and the external bolsters. Tension is exerted on the fastener sheet to gradually draw the edges of the wound toward one another. Preferably, static tension is applied by the fastener sheets to lengthen the muscles on each side of the wound, permitting the edges to come together. Upon drawing the wound edges near one another, the wound can be closed using surgical closure techniques. A bio-compatible plastic barrier is placed into the abdomen during this entire process to keep the viscera from adhering to the underside of the abdominal wall.

The components of this invention allow for the application of a static tension to stretch the retracted lateral abdominal muscles. These muscles are held in the stretched position over a period of, for example, 36 to 72 hours, during which time they gradually lengthen and relax. This step is repeated until the midline fascial edges are brought close enough to be suture closed. The stretching forces are applied without damaging fascial integrity. Once the edges of the wound have been brought together, the wound can be closed surgically.

The present method and apparatus allows for the closure of both acute and chronic open abdomens.

BRIEF DESCRIPTION OF THE DRAWINGS

FIG. 13 is top perspective view of the abdomen of the patient of FIG. 8 showing a suturing step in the abdomen closure method;

FIG. 14 is top perspective view of the abdomen of the patient of FIG. 8 showing the abdomen closed according to the present method and apparatus;

FIG. 15 is a top perspective view of a kit according to the present method and apparatus.

DETAILED DESCRIPTION OF THE PREFERRED EMBODIMENTS

Figure 1:
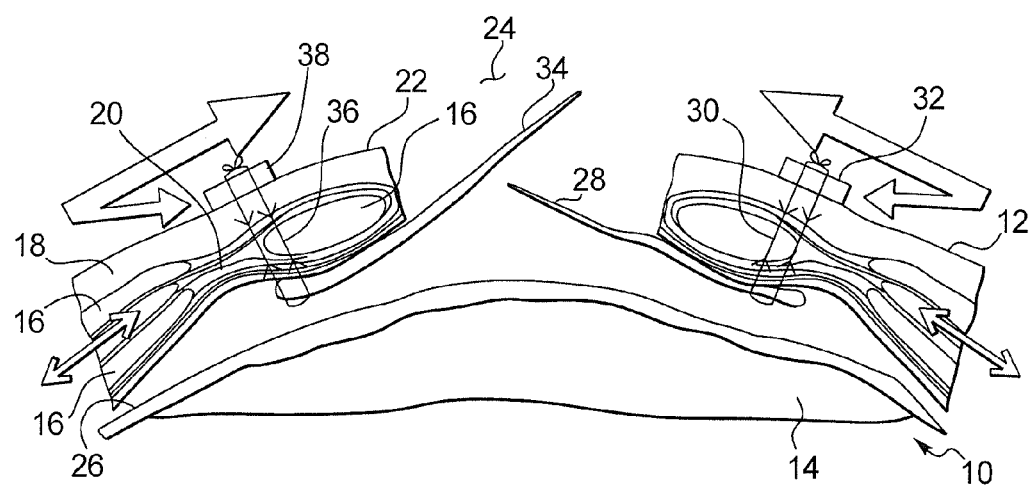
FIG. 1 is a cross sectional view through an open abdominal wound of a patient showing a method and apparatus for closing the open abdomen according the principles of the present invention.

Turning first to FIG. 1, a patient 10 has an abdominal wall 12 within which is the patient's bowel and other visceral organs 14. The abdominal wall 12 includes muscles 16, fat 18, connective tissues 20, and skin 22. An opening 24 in the abdominal wall 12 has been formed, usually by a surgical incision although it is possible the opening 24 may have been the result of an injury or otherwise.

The patient's bowel and viscera 14 may have been injured as a result of disease, accident, battlefield injury, gunshot or stab wound, or otherwise which requires the abdominal wall to be opened so that the surgeon can repair the injury, treat the disease, relieve pressure within the abdominal cavity, or for other reasons. The opening 24 in the abdominal wall 12 may not be closed at the conclusion of the initial treatment, for example if the bowel and viscera 14 are swollen, if the surgical repair or treatment requires additional steps that require opening of the abdominal cavity, or for other reasons. The result is an open abdomen wound. The open abdomen wound may remain open for days or weeks, though the internal organs are generally covered by a barrier sheet which the abdominal wall is open. During this time, the muscles 16, which include the rectus muscles as well as the transverse abdominal muscles and the lateral oblique muscles and other tissues of the abdominal wall retract laterally, so that it is no longer possible to close the wound 24 by conventional surgical techniques. In particular, the muscle fibers of the oblique and transverse muscles of the abdomen extend horizontally and after opening of the abdomen the unopposed forces of the oblique and transverse muscles cause the edges of the opening to pull away from each other and prevent the edges of the opening from being connected together again. This is referred to as loss of domain.

A common location for the surgical opening of the abdomen is between the two halves of the rectus muscle at the midline of the abdomen. The pulling forces of the oblique and transverse muscles pull the halves of the rectus muscles apart. The fascial connection between the rectus muscle halves is lost and it is desirable that the patient regain this muscle connection. The present method and apparatus seeks to restore anatomical integrity, the original anatomy, of the patient.

According to the present method, a barrier sheet 26 is placed over the bowel and viscera 14. A sheet 28 of a material having a loop structure of a hook and loop fastener is fastened in the inner surface (the peritoneal surface) of the abdominal wall 12 at one side of the opening 24. The loop sheet 28 is fastened by suture stitches 30 through the loop sheet 28, and through the abdominal wall 12 including through muscle, connective tissue, fat and skin. The suture 30 is passed through a bolster 32 that is positioned on the outside of the abdominal wall 12 on the surface of the skin 22. The suture 30 is preferably tied off on the top surface of the bolster 32. The bolster 32 acts to spread the forces that are transmitted from the loop sheet 28 through the sutures 30 over a larger area of the skin and thereby prevent the forces from being concentrated on a small area.

A hook sheet 34 is secured to the abdominal wall 12 at the opposing side of the opening 24 from the loop sheet 28. The hook sheet 34 is sutured to the inside of the abdominal wall 12 by suture stitches 36 and extend to a bolster 38 that is positioned on the surface of the skin 22. The suture 36 is tied off on the bolster 38. The hook sheet 34 is attached with the hook surface facing toward the bowel 14 and the loop sheet 28 is attached with the loop surface facing away from the bowel 14 so that the sheets 28 and 34 can be attached to one another. The sheets 28 and 34 form a hook and loop fastener sheet that resists static tension forces along the plane of the sheets and so permits the doctor to draw the opposing sides of the opening 24 toward one another and secure the sheets 28 and 34 to one another to hold the sides of the opening in place, allowing the muscles and other tissues to stretch under static tension. The tension forces exerted by the sheets 28 and 34 is distributed by the bolsters 32 and 38.

The present apparatus provides a static tensioner that applies a static pulling force to the muscles and other tissues of the abdominal wall. By applying the static tension or pulling force, the muscles that have been stretched will gradually relax. As the muscles relax, the muscles lengthen. The hook and loop sheets loosen with the lengthening of the muscle fibers, indicating to the medical personnel that the sheets can be again tensioned. The tension forces are applied in steps or blocks rather than constantly. The distribution of forces permits significant forces to be applied at each step.

The loop sheet 28 and the hook sheet 34 together form a fastener sheet. Other forms of fastener sheets are possible according to the present invention as well. For example, plastic, woven or non-woven fabric or other materials formed into sheets and need not include hook and loop fasteners. The sheets should be of sufficiently heavy material to be able to resist the tension forces. The sheets may be folded together, rolled together, gathered together, wrapped on one another, or otherwise secured to one another. A fastener may be applied to the folded, rolled, or gathered sheets to resist tension forces on the sheets. For example, the folded, rolled or gathered portions of the sheets may be stitched or sewn to one another, such as by suture. As the wound closes, further folding, rolling or gathering of the sheets together applies further tension forces to the sheets thereby applying static tension to the wound edges. The fastener to secure the sheets to one another may include clamps, laces, staples, stitches, snaps, zippers, zip fasteners, or other fastener types. In one embodiment, suture is stitched through the folded over portions of the sheets to secure them to one another and apply the tension that enables the present method and apparatus to close an abdominal wound. The fasteners preferably hold the sheets together sufficiently strongly to resist tension forces applied to the sheets by the patient's abdominal muscles. References to hook and loop fasteners herein encompass other fastener types as well.

The fastener sheets of a preferred embodiment are adjustable so that as the wound is closed, additional tightening forces can be applied. Additionally, if the need exists to release some of the pressure from the internal organs, such as during the healing process, the fastener sheets can be adjusted to permit the edges of the abdominal wound to temporarily move apart reduce pressure during the healing process.

It is envisioned that the bolster and fastener sheet apparatus could be affixed to the abdominal wall while the viscera is still in the swelled and healing state and the patient has an open abdomen. The fastener sheets could be left unfastened until the doctor is ready to close the abdominal wound. Instead, the fastener sheets could be fastened to one another at a lower tension to reduce the extent to which the abdominal muscles withdraw during the open abdomen healing stages so that less domain has to be recovered during the abdomen closing stages. With the bolsters and fastener sheets already in place, one less surgical procedure is required in the closure process.

Figure 2:
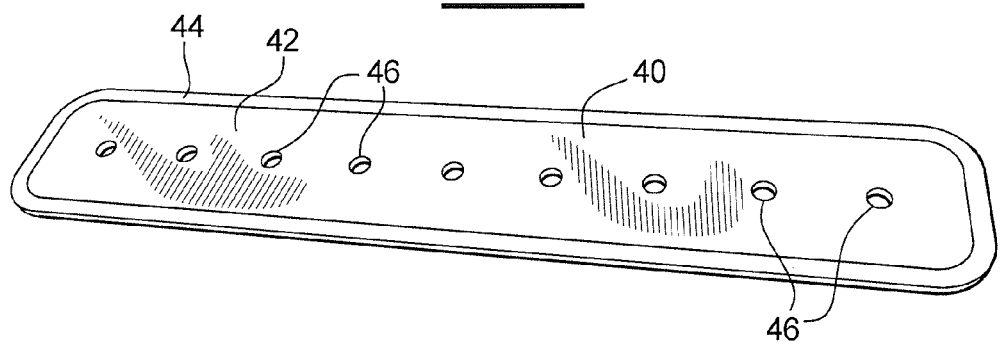
FIG. 2 is a top perspective view of a bolster as used in the present method and apparatus.

In FIG. 2, a bolster 40 of a preferred embodiment is shown. The bolster 40 includes an elongated hard strip 42 of a flexible plastic material that is set into a soft strip 44 of a cushioning material such as a foam, hydrocolloid or other soft material. In one embodiment, the soft strip is a non-latex closed cell foam. A series of holes 46 is formed in the bolster 40 through both the hard strip 42 and the soft strip 44, for example, along the centerline of the elongated bolster so that the suture is passed through the holes. In one embodiment, the holes 46 are positioned approximately one inch apart or at another appropriate distance to distribute the compressive forces when the suture knot is tightened. The material of the hard strip 42 is generally a hard plastic that resists cutting by the suture, even when subject to considerable force. The edges of the holes are preferably rounded, beveled or smoothed so as to avoid abrading the suture material. The plastic strip 42 can twist and torque without deforming and it provides a place to tie a knot in the suture. Other materials are of course possible The soft strip 44 extends a distance beyond the edges of the hard strip 42 to cushion the edges of the hard strip 42 from direct contact with the patient's skin. In one embodiment, the foam 44 extends by ⅛ to ¼ of an inch beyond the edges of the plastic strip. The corners of the bolster 40 may be rounded to avoid sharp corners that might dig into the patient's skin.

Figure 3:
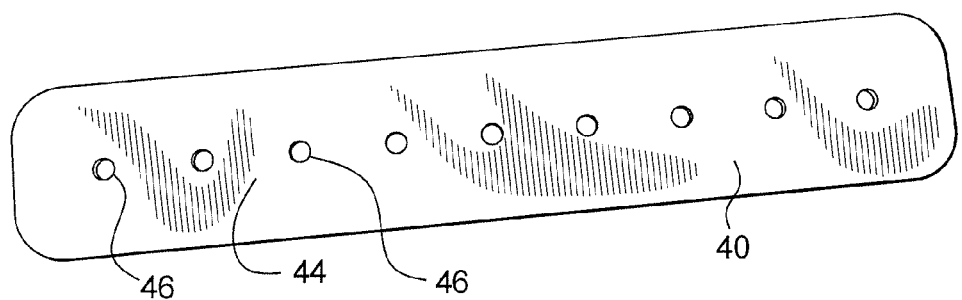
FIG. 3 is a bottom perspective view of the bolster of FIG. 2.

FIG. 3 shows the bolster 40 from the skin contact side. The soft strip 44 covers the underside of the bolster 40 completely. The holes 46 extend through the soft strip 44. The material of the soft strip 44 is a biocompatible material.

Figure 4:
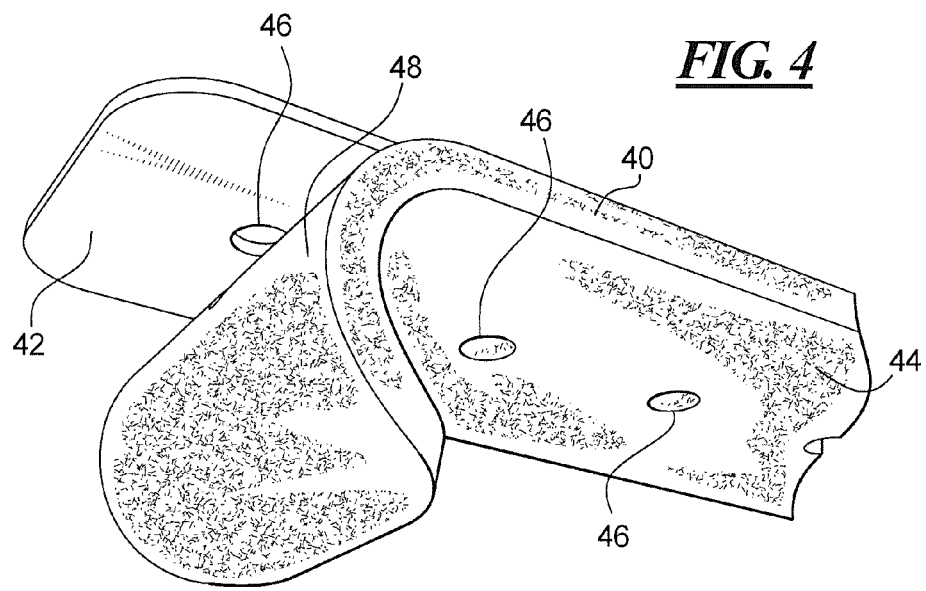
FIG. 4 is an enlarged bottom view of an end of the bolster of FIG. 2.

Turning to FIG. 4 the bolster 40 is shown from the bottom with a person pulling the soft strip 44 away from the hard strip 42 to reveal a slight recess 48 in the soft strip 44 into which the hard strip 42 fits. The foam strip 44 is glued to the hard strip 42 except that an approximately one half to one inch portion at the ends of the hard strip 42 are not glued to the foam 44. It is also possible that the hard strip 42 presses an indentation in the soft strip 44 or sits on top of the soft strip. The hard strip 42 and soft strip 44 may be molded together or glued together or otherwise affixed to one another. As shown in the figure, the soft strip 44 can be readily pulled from the hard strip 42. This permits the bolster 40 to be more easily trimmed or shortened as needed.

Figure 5:
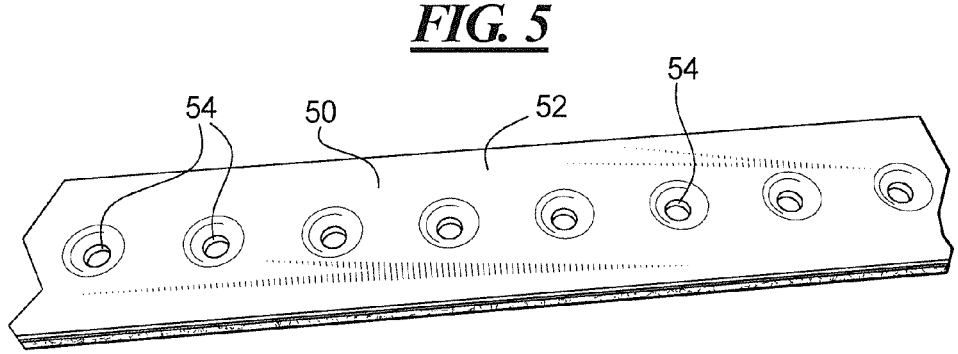
FIG. 5 is a top view of a second embodiment of a bolster for use in the present method and apparatus.
Figure 6:
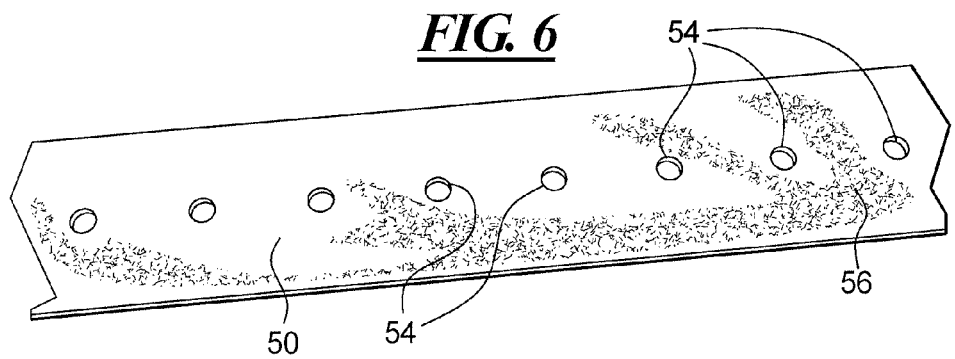
FIG. 6 is a bottom view of the second embodiment of the bolster of FIG. 5.
Figure 7:
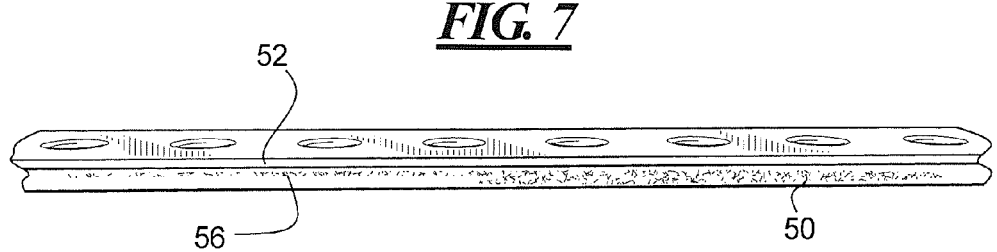
FIG. 7 is a side view of the second embodiment of the bolster of FIG. 5.

An alternative embodiment of a bolster 50 is shown in FIG. 5. The bolster 50 includes an elongated metal strip 52, that in one embodiment is of aluminum although other materials may be provided instead. The metal strip 52 has a series of holes 54 generally along its centerline. The bolster 50 is shown from the underside in FIG. 6. The underside is formed of foam 56. The foam strip 56 cushions the bolster 50 to prevent contact between the patient and the metal backing strip 52. A side view of the bolster 50 is shown in FIG. 7. The metal strip 52 on the top surface is relatively thin so as to be flexible yet hard so as to prevent pull-through by the sutures.

The foam strip 56 or other cushioning material is relatively thicker than the metal strip 52 and preferably several times thicker. The metal strip 52 and foam strip 56 may be secured to one another by glue that can be peeled apart. As the bolster is shortened during the progression of the treatment, the foam can be cut off and the metal strip can be coiled up at the ends should the bolster need to be shortened.

Bolsters of two different configurations have been shown. Other shapes, sizes, proportions, and materials of bolsters are also possible and are within the scope of the present invention. Utilization of the bolsters in conjunction with securing of the bolsters and fastener sheets through the abdominal wall, preferably laterally of the rectus muscles, enables a maximum tightening force to be applied to the abdominal wall to provide the greatest extent of closing to the wound in the shortest time. The bolsters and fastening arrangement enable the application of static tension forces that allow the muscles of the abdominal wall to both relax and lengthen.

The use of the bolsters with the through-the-abdominal-wall attaching technique provides a fascial preservative technique in which the tissues at the edges or fascia of the wound are retained substantially without damage and with little loss of the tissues. The bolsters are attached with regularly spaced sutures as a result of the holes formed therein, providing a distribution of the forces on the abdominal wall to avoid tissue damage.

Figure 8:
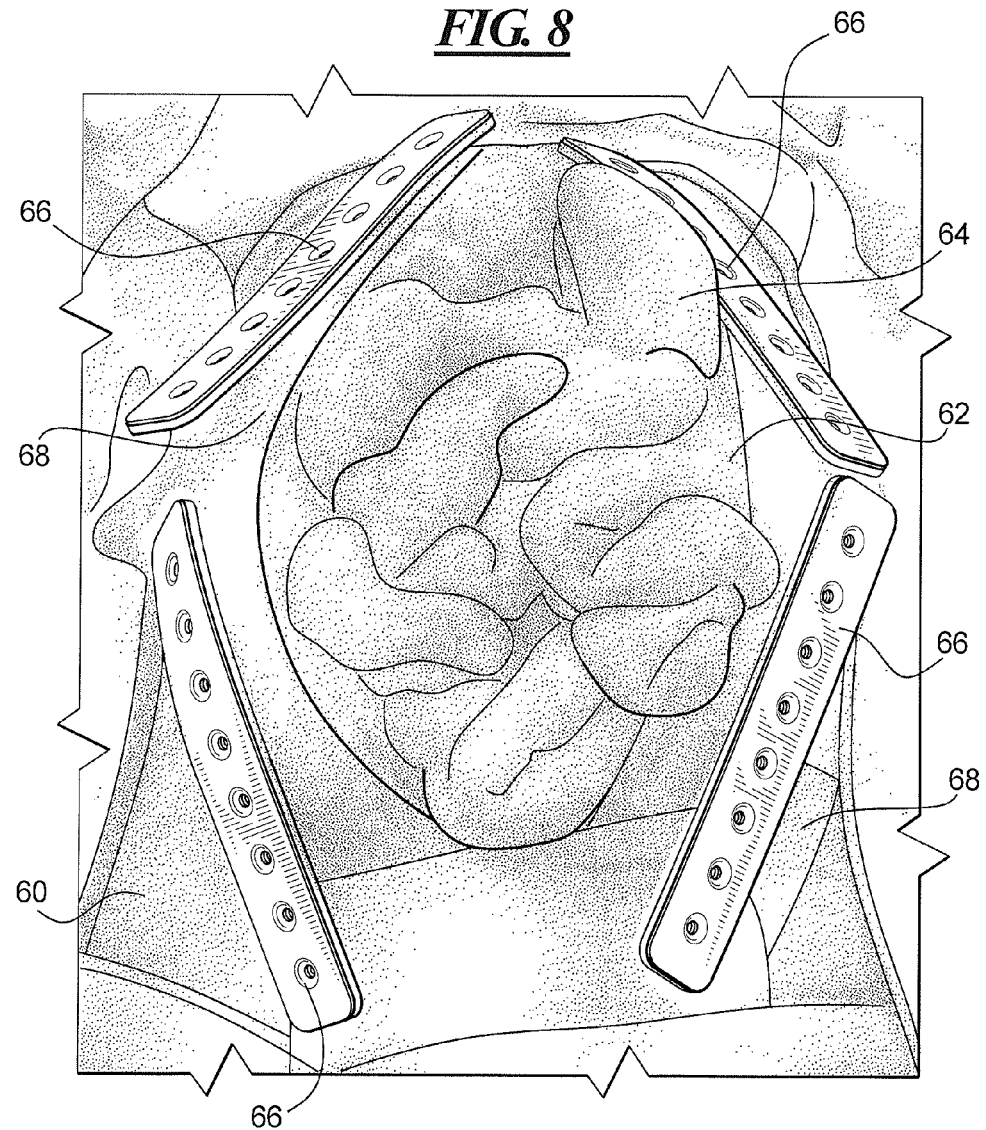
FIG. 8 is a top perspective view of an abdomen of a patient with an open abdomen wound that is being prepared for closure using the present method and apparatus.

In FIG. 8, a patient 60 has had a medical issue that has caused swelling of the viscera within the abdominal cavity. The medical issue may be, among other things, abdominal compartment syndrome, complex abdominal trauma, profound acidosis, or other causes. The patient has been given a laparotomy, also known as a celiotomy, which is a large incision in the abdominal wall to gain access to the abdominal cavity. In the illustrated example, the patient has been given a midline incision 62. Pressure and tissue swelling within the abdominal cavity has caused the bowel 64, including the large and small intestine to extend out of the incision (bowel distension), here the result of a condition known as edematous bowel, which may have resulted from a severe motor vehicle crash, for example. The incision 62 relieves the pressure within the abdominal cavity, referred to as a decompressive laparotomy, to thereby prevent the pressure from causing tissue death within the abdominal cavity. However, the incision cannot be closed until the swelling of the viscera decreases and the viscera 64 can be put back into the abdominal cavity.

Bolsters 66 are positioned on either side of the incision to begin the closure of the open abdomen. The bolsters 66 are preferably placed atop hydrocolloid sheets 68 so that a barrier is provided between the patient's skin and the bolsters 66. The bolsters 66 are positioned with the soft material side against the patient and the hard side away from the patient.

Figure 9:
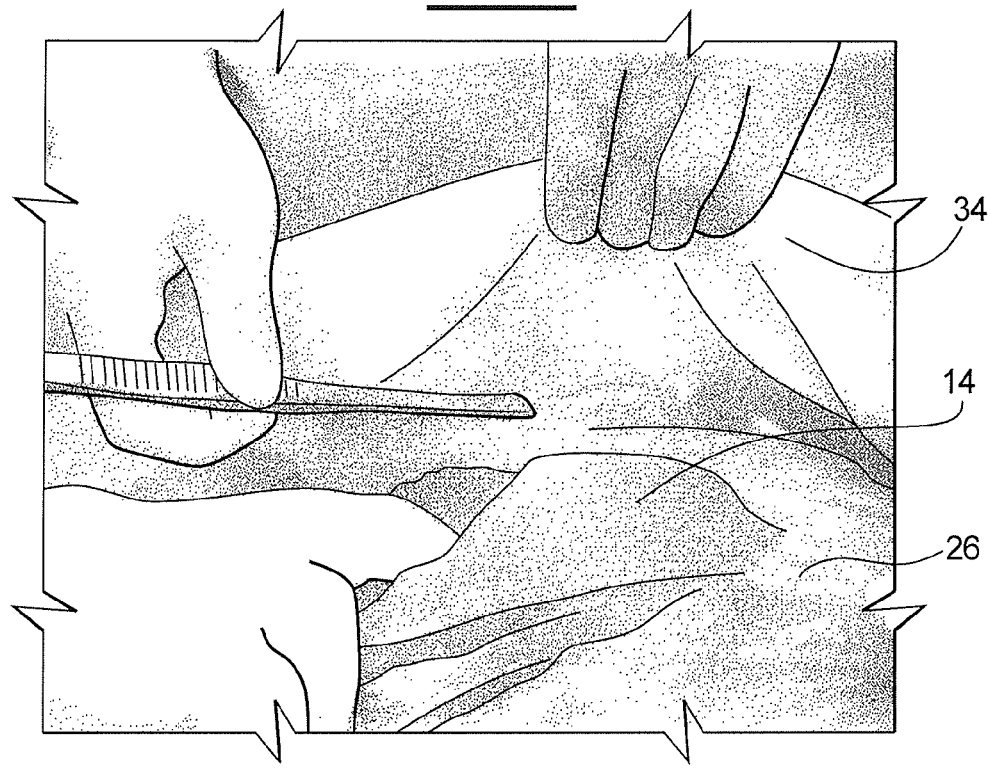
FIG. 9 is a top perspective view of the abdomen of the patient of FIG. 8 showing a step in the abdomen closure method.

In FIG. 9, the viscera or bowel 14 is covered with an abdominal dressing 26, which is preferably a biocompatible plastic barrier to keep the viscera from adhering to the underside of the abdominal wall. The hook sheet 34 and on the other side of the wound (which is not visible in this view) the loop sheet 28 are positioned over the biocompatible barrier and are sutured into place by sutures extending through the abdominal wall and through the bolsters. The hook and loop sheets 34 and 28 and the bolsters 66 (also not visible in this view) are positioned so as to be at or adjacent the rectus muscle of the patient for midline incisions. Typically, the hook and loop sheets or other fastener sheets extend under the abdominal wall several inches from the edges of the wound. The sutures pass through all the layers of the abdominal wall. The suture threads are tied in knots that rest on the bolsters 66. The hook and loop sheets are compressed together to engage the hooks and loops to one another to form a closure. Other types of fastener sheets use other techniques for fastening the fastener sheets to one another. In its most common embodiments a negative pressure dressing is placed over the hook sheet and loop sheet closure and negative pressure is applied.

Figure 10:
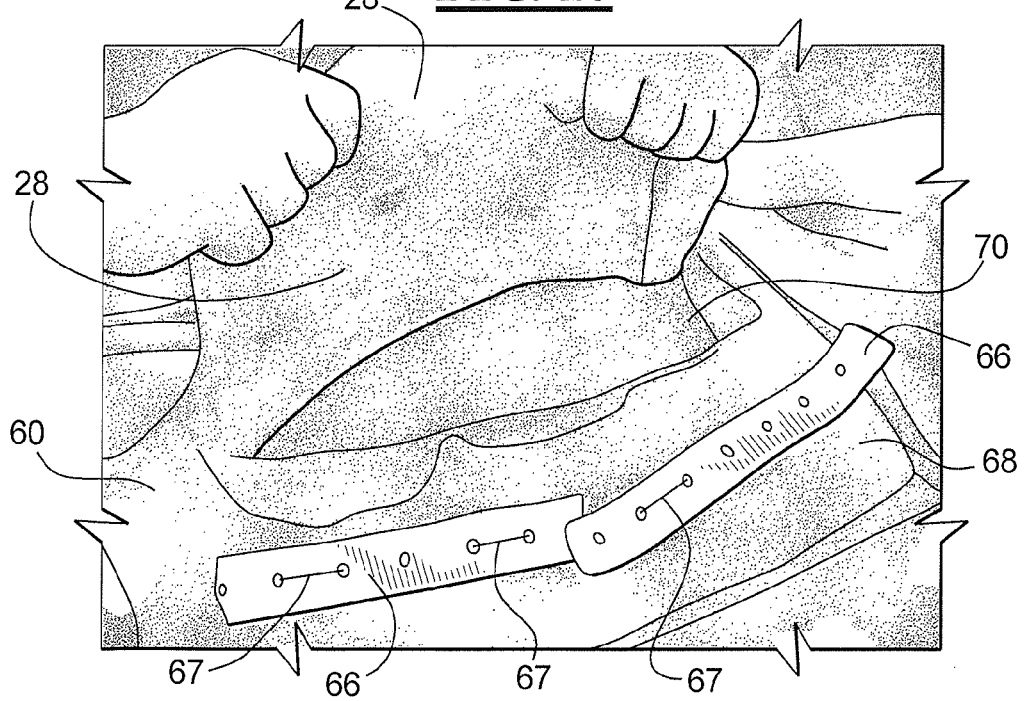
FIG. 10 is top perspective view of the abdomen of the patient of FIG. 8 showing another step in the abdomen closure method.

With reference to FIG. 10, the hook and loop fastener sheets 34 and 28 have been attached to the patient 60 using the bolsters 66 to spread the force of the sheets on the patient's tissues. The bolsters 66 are attached with loops of suture 67 that extend through holes in the bolsters 66 and through the abdominal wall to secure the fastener sheets in place on the underside of the abdominal wall. The suture loops 67 are knotted on the top surface of the bolsters 66. The doctor is pulling on one of the hook and loop sheets 34 and 28 to stretch the muscles and tissues of the abdominal wall so that the edges or fascia 70 of the wound can be drawn toward one another. The stretching of the muscles and tissues to its original anatomical position is a gradual process that is typically performed in stages, with the fastener sheets applying static tension to the tissues for a time between each application of additional tension to permit the tissues to stretch and the muscles to lengthen.

Figure 11:
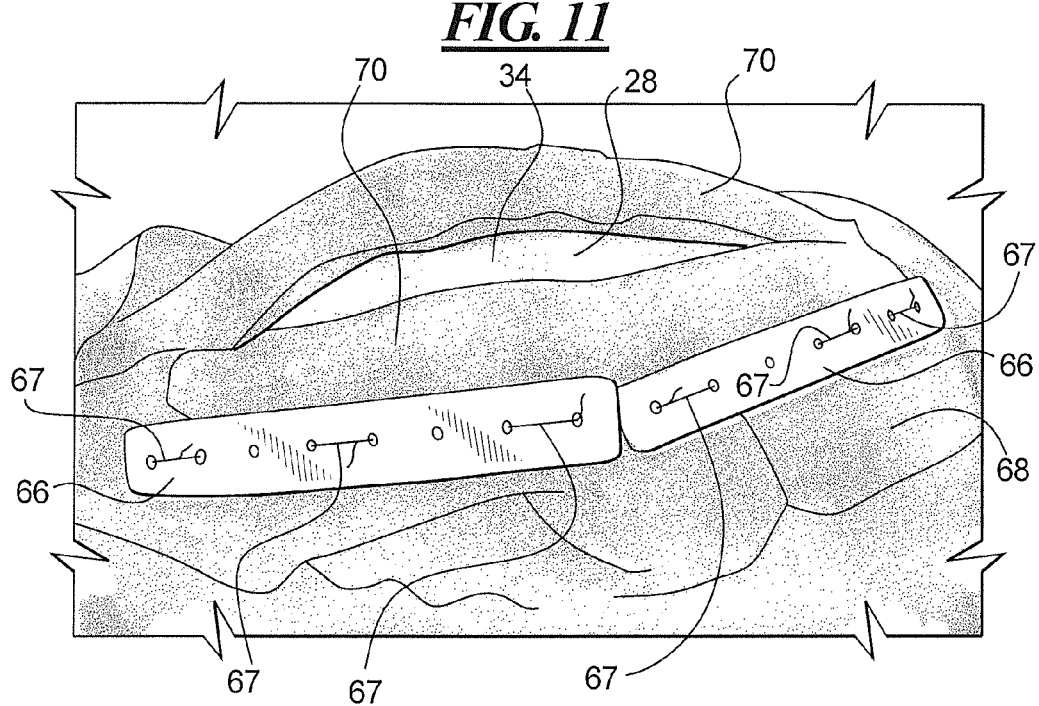
FIG. 11 is top perspective view generally from the side of the abdomen of the patient of FIG. 8 showing an intermediate stage in the abdomen closure method.

Turning to FIG. 11, the hook and loop sheets 34 and 28 are anchored along the edges of the wound with the bolsters 66. The loops of suture 67 are in the illustrated embodiment positioned at regularly spaced locations along the edges of the wound and along the bolsters 66. Here, the loops 67 extend through adjacent holes in the bolsters 66, although other arrangements of suture loops may be made as desired by the doctor. A strong tension force is exerted on the tissues of the abdominal wall by the attachment of the hook and loop sheets 34 and 28 to one another which is the result of the tension applied by the doctor and the fastening of the sheets together while under tension. The fastener sheets apply a static tension to the tissues, as a result of which the muscles and tissues of the abdominal wall are stretched so that the wound is made smaller and the edges or fascia 70 are brought closer together. The bolsters 66 and the looped sutures 67 distribute the forces of the hook and loop fasteners 34 and 28 or other fastener sheets without damage to or loss of tissue at the edges of the wound, in other words without loss of domain.

Figure 12:
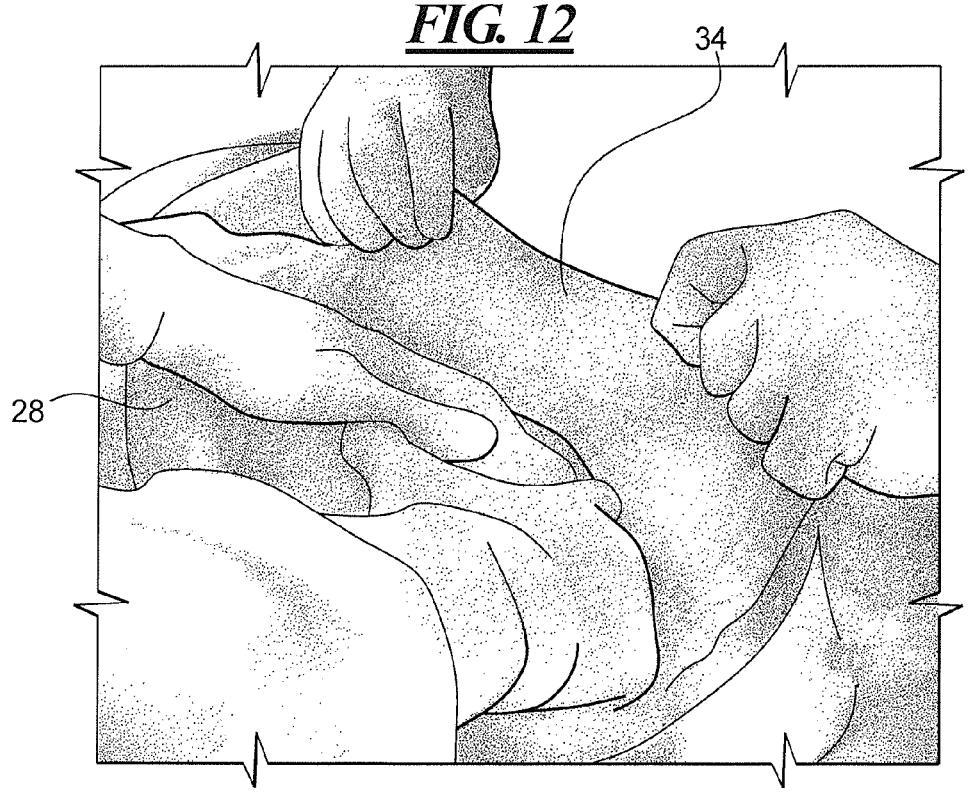
FIG. 12 is top perspective view of the abdomen of the patient of FIG. 8 showing a further step in the abdomen closure method.

In FIG. 12, the closing of the wound is progressive with further closure being accomplished in steps. Here, one doctor is pushing the loop fastener sheet 28 in one direction to exert tension on one edge 70 of the wound while a second doctor pulls the hook fastener sheet 34 up and then over to engage the two sheets with one another to further close the wound. Over the course of one or several steps, the edges or fascia 70 of the wound are brought sufficiently close to permit the wound to be closed by surgical methods.

FIG. 13 shows a wound 24 that has had the opposing edges or fascia 70 brought sufficiently close to one another that surgical joining of the edges of the wound can proceed. The hook and loop fasteners 34 and 28 and the bolsters 66 remain in place as surgical rejoinder is begun to prevent loss of the progress made during the closing steps. When the tissues of the abdominal cavity are reattached to one another, the bolsters 66 and hook and loop fasteners 34 and 28 are removed and the closure of the wound is completed.

For wounds in which the periphery of the wound is large yet as the wound is brought to a close position, the bolsters may need to be shortened as the closing progresses. The bolsters formed of the plastic strip and foam can be cut by surgical instruments as shortening is required. For the embodiments of the bolsters formed of foam and a metal strip, the foam is cut from the end of the bolster and the end of the metal strip that overlaid the foam is cut away or coiled so that it is out of the way In FIG. 14, the patient 60 shown in this procedure has had the wound 24 closed. The abdominal walls edges 70 have been drawn together and the tissues at the edges of the wound have retained their integrity during the tensioning process so that the closure doesn't have to accommodate tissue loss at the edges of the wound. A single midline scar 72 will result without the need for a skin graft to cover the viscera. Drain tubes 74 remain extending through the abdominal wall on a temporary basis following the surgical closure to permit any fluids to drain. The patient 60 can now proceed with the healing process with a closed abdomen, without the need for a skin graft over the viscera, and without the risk that would be involved in closing the abdomen while the viscera was in the swollen state. The rectus muscles are reattached so that the patient is no longer functionally impaired.

FIG. 15 shows a kit 80 of components used by the doctor in performing the method as shown. The kit of the preferred embodiment includes four bolsters (two of which are shown, which are to be cut in half to make four bolsters) 66, a hook and loop fastener sheet set 82, four or more adhesive sheets of hydrocolloid dressing 84, and a polyurethane bio compatible viscera protecting barrier 86 to be inserted into the abdomen while the device is in place. The kit also includes directions to the doctor to ensure proper use of the components of the kit. Suture for fastening the bolsters 66 and hook and loop sheets 82 is recommended to be a number 5 braided polyester suture (such as sold under the trade names Ethibond or Tycron) A negative pressure dressing such as the one made by KCI or Smith and Nephew is recommended to be used as a topical dressing.

Other components may be provided in the kit as well. For example, the kit may include more than four bolsters or fewer than four bolsters. Other types of dressing sheets and barriers may be provided instead of those mentioned above, or these may be left out with the doctor providing his or her own choice of barrier and dressing. Needles may be provided in the kit and the kit may even provide the suture thread to be used to attach the hook and loop sheets and the bolsters to the patient.

Figure 16:
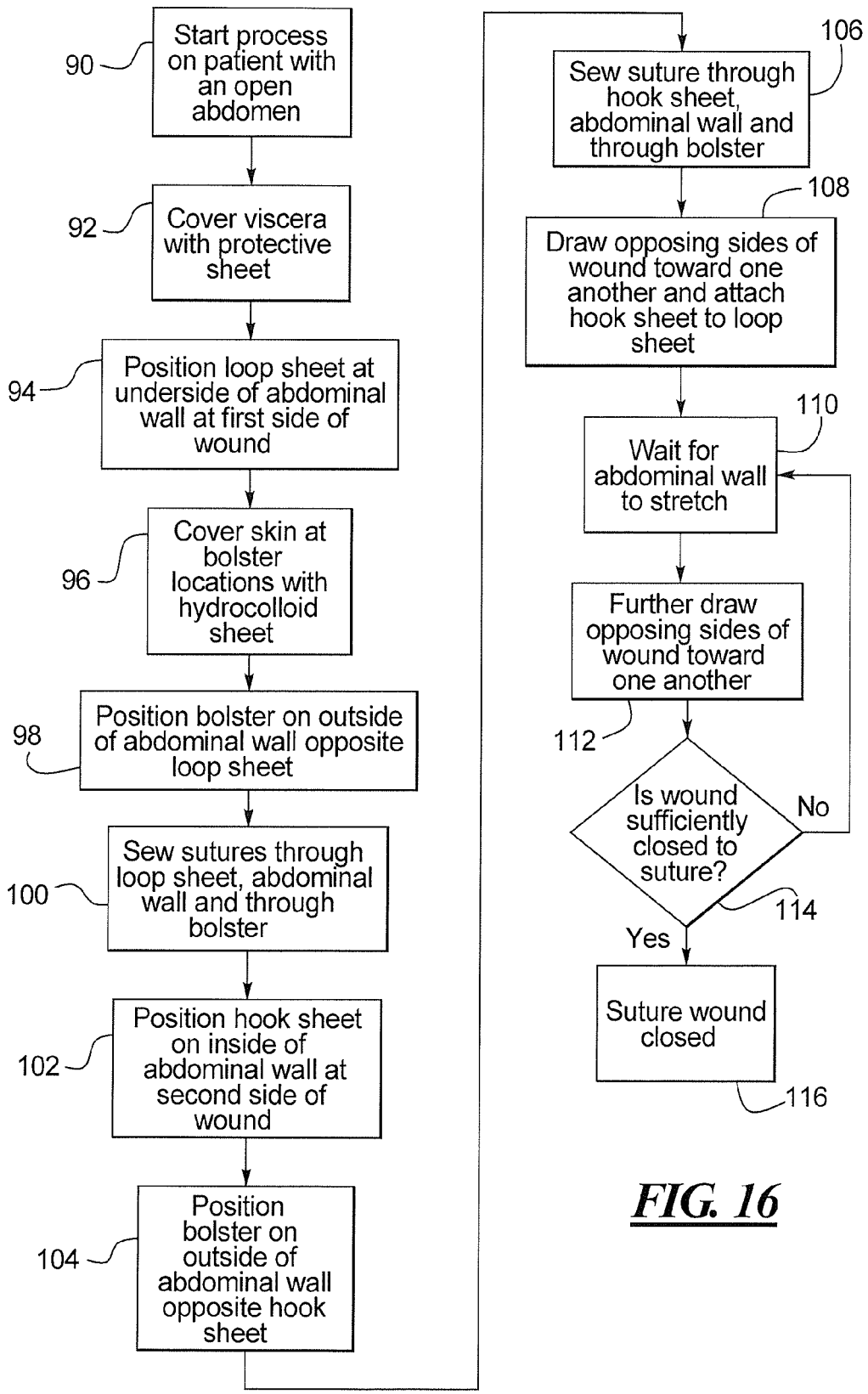
FIG. 16 is a flow chart showing steps in the present method.

A flowchart of steps according to the present method is shown in FIG. 16. The steps according to one embodiment of the method include a step 90 begins the process with a patient who has an open abdomen wound by prepping the patient and bringing them into an operating room if not already there as a result of a prior procedure. In step 92, the viscera including the bowel and other organs that are exposed as a result of the open abdomen are covered by a protective sheet. Step 94 provides that the loop sheet is positioned at the underside or inside of the abdominal wall along a first side of the wound. With a midline incision, the loop sheet is inserted at least to the outer edge of the rectus muscle. Step 94 starts with positioning the loop sheet, but the doctor may chose to begin with the hook sheet instead. The order of the steps set forth here provide one example and other orders of steps may be performed and are within the scope of the invention.

In step 96, the skin along the edges of the wound are covered with a protective sheet such as a hydrocolloid sheet. Other protective materials such as sheets or barriers may be provided as desired. The hydrocolloid sheet or other material may be applied only to the first side in this step, or two both sides of the wound. This step may be performed sooner in the process, so long as the hydrocolloid sheet or other material is in place, if desired, prior to the attachment of the bolsters.

In step 98, the bolster is positioned on the outside of the abdominal wall along the first edge of the wound and opposite a portion of the loop sheet that has been positioned inside the abdominal wall. In a midline incision, the bolster is positioned to the outside of the rectus muscle, which typically is about two inches from the edge of the wound.

Sewing or suturing of the loop sheet with sutures that extend through the abdominal wall is carried out in step 100. The suture material is passed through an opening in the bolster, then through all the layers of the abdominal wall and through the loop sheet using a needle. The suture is brought back through the loop material a distance from the initial stitch and is brought through all the layers of the abdomen and through another opening in the bolster using the needle. The suture may be tied off on top of the bolster material so that a loop of the suture extends through the bolster and abdomen wall and loop material. Another loop of suture is formed by the same technique in an adjacent pair of holes in the bolster. The suturing of the loop material continues along the length of the bolster. The doctor may form suture loops through each adjacent pair of holes in the bolster or may skip holes as desired. It is also possible that the doctor may choose to form a running stitch through several bolster holes or may use other stitching techniques.

After the loop sheet has been installed, the hook sheet is installed in much the same way as the attachment of the loop sheet. In step 102, the hook sheet is positioned on the inside of the abdominal wall along the second side of the wound. The hook sheet edge is inserted to an outer edge of the rectus muscle in the example. As noted above, the hook sheet may be installed first before the loop sheet. The bolster is positioned on the outside of the abdominal wall on the hydrocolloid sheet in step 104. As noted for the loop sheet, in the example, the bolster is positioned at the outside edge of the rectus muscle. Step 106 has the doctor sewing the hook sheet and bolster to the abdominal wall using the techniques noted above.

Two bolsters may be positioned along each side of the wound so that the curved or arced edge of the wound is accommodated while the wound is wide open by positioning the bolsters at an angle to one another. As the wound is closed and the edges become more linear, the angle between the two bolsters decreases until they are generally in alignment with one another. A single bolster may be provided on each side of the wound, or three or more bolsters may be provided on each side as desired.

With the bolsters and hook and loop sheets in place, tension is exerted on the sheets to draw sides of the wound toward one another, as shown in step 108. The reinforced connection of the sheets to the abdominal wall provided by the bolsters enables the doctors to exert a great deal of tension force on the abdominal wall to really stretch the muscles so as to regain domain without damage to the tissues at the edges of the wound. In some embodiments, the doctor can actually lift the patient from the operating table by pulling on the hook or loop sheet. While applying the tension forces to the sheets, the doctor affixes the hook sheet to the loop sheet.

After the hook and loop sheets have been attached under tension, the patient leaves the operating room and is given time for the muscles to stretch to bring the edges of the wound closer to one another at step 110. This time may vary depending on the patient, the length of time that the patient had the open abdomen (such as whether the open wound is the result of an earlier closure by a skin graft or if it is the result of a recent medical procedure) and other factors. In step 112, the patient is returned to the operating room, the hook and loop sheets are disconnected from one another and further tension forces are exerted on the sheets to further pull the edges of the wound toward one another. If the wound is not sufficiently closed to close the wound surgically, as determined in step 114, the process returns to step 110 waiting for the abdominal wall to stretch.

Further tensioning steps are applied as needed until the wound is closed sufficiently to permit the doctor to surgically close the wound. If the determination has been made at step 114 of sufficient closure, the wound is sutured closed at step 116. The protective sheet, the hook and loop fasteners and the bolsters are removed as the wound is closed. The patient may now continue healing with a closed abdomen.

The distribution of the forces from the hook and loop fastener sheets by the bolsters prevent damage to the tissues at the wound edge. Tissues are not lost during the closure process, speeding the closure process. The bolsters work with the hook and loop sheets to close the wound.

Thus, an open abdomen wound as a result of injury or surgery is closed using hook and loop fastener sheets or other fastener sheets that are attached at opposing edges of the wound using bolsters through which surgical suture thread is passed to secure the abdominal wall between the fastener sheets and the bolsters. Tension forces are exerted on the fastener sheets and the sheets secured to one another in one or more steps drawing the wound edges toward one another. The tension forces are distributed along the length of the bolsters to avoid loss of tissue at the wound edges. The static tension applied by the fastener sheets to the retracted lateral muscles of the abdomen allow the muscles to be stretched to a new relaxed position so that the open abdomen can be sutured closed. The muscles are restored to their correct anatomical position. The distribution of forces through the use of the bolsters prevents damage to the fascial edges of the wound to provide a definitive fascial closure. Successful closure of the wound is thus possible.

Although other modifications and changes may be suggested by those skilled in the art, it is the intention of the inventor to embody within the patent warranted hereon all changes and modifications as reasonably and properly come within the scope of his contribution to the art.

I claim:

1. A method for closing an open abdomen wound, comprising the steps of:
    positioning a first bolster along a first edge of the abdominal wound;
    securing a first fastener sheet to the first edge of the wound by suturing through the first fastener sheet and through the abdominal wall and through the first bolster to secure the abdominal wall between the first fastener sheet and the first bolster;
    positioning a second bolster along a second edge of the abdominal wound;
    securing a second fastener sheet to the second edge of the wound by suturing through the second fastener sheet and through the abdominal wall and through the second bolster to secure the abdominal wall between the second fastener sheet and the second bolster;
    applying tension to at least one of said first and second fastener sheets to draw the first and second edges of the wound toward one another;
    attaching said first fastener sheet to said second fastener sheet while under tension so as to apply static tension to opposing sides of the abdominal wound;
    repeating said steps of applying tension to at least one of said first and second sheets and attaching said first and second sheets to one another as needed to draw the first and second edges of the wound in proximity; and
    surgically closing the abdominal wound by suturing the first and second edges to one another.

2. A method as claimed in claim 1, wherein said first and second fastener sheets include a hook fastener sheet and a loop fastener sheet.

3. A method as claimed in claim 1, further comprising the steps of:
    applying a hydrocolloid sheets on skin of the abdomen; and
    wherein said step of positioning the bolsters positions the bolsters on the hydrocolloid sheets.

4. A method as claimed in claim 1, wherein said step of positioning said bolsters follows positioning of the first and second fastener sheets.

5. A method as claimed in claim 1, where said bolsters are positioned at or adjacent a patient's rectus muscles.

6. A method as claimed in claim 1, wherein steps of securing the first and second fastener sheets includes suturing through all layers of the abdominal wall.

7. A method as claimed in claim 1, wherein said step of steps of securing said first and second fastener sheets includes the sub-steps of:
    sewing a suture:
        through a first opening in a first of said bolsters,
        through the abdominal wall,
        through the fastener sheet at a first location,
        back through the fastener sheet at a second location,
        back through the abdominal wall, and
        through a second opening in said first bolster that is spaced from said first opening;
    tying ends to said suture that extends from the first opening and from said second opening to one another to form a loop of suture affixing the fastener sheet to the bolster through the abdominal wall;
    repeating the sewing and tying steps at further pairs of openings in the first bolster to form loops of suture along a length of the first bolster; and
    repeating the sewing and tying steps with a second bolster.

8. A method as claimed in claim 7, wherein said first bolster is formed of a soft inner material and a hard outer material, and wherein said step of tying the ends of the suture positions in a knot of suture that is on the hard outer material of the first bolster.

9. A method as claimed in claim 7, wherein said loops of suture are substantially evenly spaced along a length of the bolster.

10. A method for stretching retracted lateral muscles of a patient's abdomen, comprising the steps of:
    positioning bolsters on the patient's abdomen;
    affixing first and second fastener sheets to said bolsters, said affixing step including suturing through at least portions of the patient's abdominal wall and through the fastener sheets and through the bolsters;
    exerting a tension force on at least one of said fastener sheets; and
    fastening said fastener sheets to one another so as to exert a static tension force on the lateral muscles of the patient's abdomen.

11. A method as claimed in claim 10, further comprising the step of: repeating the steps of exerting a tension force and fastening said fastener sheets to further stretch the retracted lateral muscles.

12. A method as claimed in claim 10, further comprising the step of: surgically closing an open abdomen after stretching the retracted lateral muscles of the patient's abdomen.

* * * * *